United States Patent [19]

Miller

[11] Patent Number: Plant 6,794

[45] Date of Patent: May 9, 1989

[54] PHILODENDRON PLANT NAMED BARON

[75] Inventor: Howard N. Miller, Gainesville, Fla.

[73] Assignee: Cora McColley, Orlando, Fla.

[21] Appl. No.: 146,776

[22] Filed: Jan. 21, 1988

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Frank B. Robb

[57] ABSTRACT

There is disclosed a compact semi-self-heading Philodendron plant of unusual growth habit, since it will remain stocky with thick leathery emerald green, round leaves on short petioles with minimum forcing, being self-heading likewise and if grown on a pole and fertilized frequently, it becomes a striking totem specimen, the growth as a totem being slow, this providing a desirable feature since the plant will not stretch or become leggy thereby.

1 Drawing Sheet

BACKGROUND AND DESCRIPTION OF THE INVENTION

My present invention comprises a new and distinct variety of Philodendron Plant which is the result of crossing an unnamed rosette seedling whose parentage included *Philodendron hastatum, Philodendron wendlandii, Philodendron imbe* and an unnamed seedling from the breeding program with Philodendron Emerald Duke, U.S. Plant Pat. No. 3,397. In turn this program was continued by crossing a seedling of the above with the species *Philodendron glaucophyllum.* From this latter cross a single seedling was propagated by tissue culture and is the embodiment of this invention.

In the vicinity of Orlando, Fla., an extensive program of philodendron hybridizing has been carried on and is being directed toward developing tough, leathery, philodendron plants which are compact, for the most part, self-heading, excellent growers and keepers in in-house conditions. There is also some demand for tall growing totems and the emphasis by me has been to produce new types and textures of plants with more colors than previously available.

Further the program of breeding is emphasizing production of Philodendrons which will resist disease and insect problems requiring only low in-house maintenance.

In view of the increasing emphasis currently on interior landscaping, there is great demand for new types of Philodendron with distinctive color, form and growth habit. My breeding program has these objectives as a goal.

The philodendron of the instant invention is a very tough, durable, compact self-heading, free standing plant, or if by design and with increased fertilizer and care it will slowly grow into a stalked plant that is adapted for use with support as a totem.

I have chosen to call this plant "Baron" for commercial identification.

I have caused this new variety to be asexually reproduced from cloning through tissue culture and although older plants do produce a stocky stem if trained on a support, the amount of vegetative material is negligible for mass reproduction. The plant described herein has been found to retain its distinctive characteristics through successive tissue culture reproduction.

My new variety has also been exposed to various kinds of conditions in several locations and found to maintain its form and color under a wide range of light, temperature and moisture. It maintains its waxy, emerald green color best at 1000 to 1500 foot candles and performs best when grown on the dry side. For these reasons it is an excellent indoor foliage plant.

The new plant is distinctive from other philodendrons in cultivation and is not described by Graf, Bailey or Das Pflanzenreich. While my variety has some of the characteristics of certain hybrids, in most respects it is substantially different from other species and varieties. It may be most nearly compared to philodendron Emerald Duke of the U.S. Plant Pat. No. 3,397 referred to hereinbefore. However this new variety has thicker, more waxy round leaves. The growth habits of the two plants are very different.

In summary, my new variety is a compact, open rosette-like plant that can be maintained as a free-standing specimen. With special care and maintenance as before suggested, older plants can be grown on short totem plants as a stalked plant where growth is slow.

The new variety is visually distinguished by the following characteristics, including a nearly circular leaf with modified cordate base, the extended lobes coming almost together, and a cuspidate tip. The margin of the leaf is entire.

The leaves have pinnate venation with large flattened pale green midribs. The leaves are thick, tough, leathery and dark emerald green. The width of the leaf and the length, except for the protrusion of the basal lobes, are equal.

The leaf petioles are semi-erect to erect, round with flat, slightly concave upper surfaces. Petioles are approximately three fourths the length of the leaves. The internodes are one half to one inch.

The most distinctive aspect of the new variety, compared to the older standards is its growth habit, toughness, low maintenance requirements and its keeping quality.

This new plant is not considered a true rosette. Older plants may have a short stalk, but the petioles are superimposed very closely on the stem. Since the leaves are large (broad) and the lower petioles are semi-erect, the plant appears very compact. Two or three mature plants in a 10" pot will make a plant that is approximately three times as wide as it is tall.

Growth from tissue culture is uniform and of good substance and under good growing conditions is fast.

The average height of year old plants is 12"-14"; width 20"-24". Growth of these plants can be easily regulated by manipulating the water and fertilizer. The plants do not become leggy or show adverse conditions even though somewhat neglected.

The growth of the plant is excellent. It is a good specimen plant, will grow in lower light, tolerate drying, low fertilizer and retain its desired color, form and shape longer than many philodendrons known to be currently available. This new variety is resistant to bacterial leaf rot and fungal leaf spots.

I have established that my new variety will survive three to four weeks in different light intensities under normal in-house conditions without watering or fertilizing and will not wilt. In fact this plant performs best indoors with minimum care.

For commercial purposes this plant should be asexually produced from tissue culturing.

The accompanying drawing forming a part of this disclosure, shows a typical plant of the new variety in color with the colors being as nearly true as possible in illustrations of this character made by photographic means.

Color references are made to the Munsell Color Cascade published by MacBeth, Division of Kollmorgen Company, with observations recorded by daylight illumination under vinyl of not more than 30% shade.

FORM CHARACTERISTICS

Leaf shape: Round when mature and immature.

*Tip.*—Acute; Base sagittate when mature and immature.

*Displacement.*—Undulate; margin — entire.

*Venation.*—Pinnate, sunken, broad, flat, prominate midribs.

Leaf attachment: Petiolate.

Leaf arrangement: Alternate; horizontal to slightly vertical.

Petiole: Three fourth leaf length, horizontal to semi-erect, round, flat slightly concave upper surface.

Leaf texture: Firm; thick; leathery and glossy.

SIZE CHARACTERISTICS OF TYPICAL MATURE PLANT

Leaf: Width-widest point 10"-11". Width-one inch from top 4"-5".

*Length.*—12"-13".

*Thickness.*—0.10 cm.

Petioles:

*Length.*—9"-10".

*Diameter (center).*—$\frac{1}{2}$"-$\frac{3}{4}$".

*Internode spacing.*—$\frac{1}{2}$".

*Stem diameter.*—$\frac{1}{4}$".

COLOR CHARACTERISTICS

Leaf:

*Mature.*—Top 21-15 Dark emerald green. Bottom—22-13 Olive green.

*Immature.*—Top 22-12 Olive green. Bottom 22-11 Light olive green.

Leaf venation:

*Midribs.*—21-13 Olive green.

*Veins.*—21-14 Dark olive green.

Stem: 19-11 Light olive green.

Petioles: 19-11 Light olive green.

I claim:

1. A new and distinct variety of Philodendron plant substantially as herein shown and described, characterized particularly as to novelty by its stocky growth habit, as a compact, self-heading, free standing plant with thick, leathery, dark emerald green, round leaves and short petioles, as an excellent in-house plant having the ability to withstand moderately low light, low maintenance and long periods without water, and its contrasting ability to be grown with training and with increased nutrition and higher light intensities as a totem pole specimen, the plant further having a high degree of resistance to diseases and physiological problems, good keeping qualities, the leaves being broad and the petioles semi-erect, causing the plant to appear very compact with two or three of the plants grown in a ten inch pot providing the appearance of a single plant that is approximately three times as wide as it is tall.

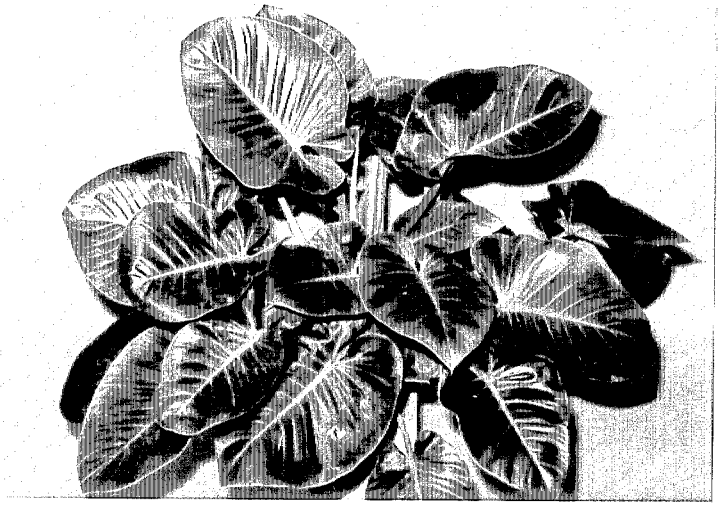

* * * * *